(12) United States Patent
Giovenzana et al.

(10) Patent No.: US 7,186,400 B2
(45) Date of Patent: Mar. 6, 2007

(54) MULTIDENTATE AZA LIGANDS ABLE TO COMPLEX METAL IONS AND THE USE THEREOF IN DIAGNOSTICS AND THERAPY

(75) Inventors: Giovanni Battista Giovenzana, Milan (IT); Giovanni Palmisano, Milan (IT); Massimo Sisti, Milan (IT); Camilla Cavallotti, Milan (IT); Silvio Aime, Milan (IT); Luisella Calabi, Milan (IT)

(73) Assignee: Bracco Imaging S.p.A., Milan (IT)

( * ) Notice: Subject to any disclaimer, the term of this patent is extended or adjusted under 35 U.S.C. 154(b) by 165 days.

(21) Appl. No.: 10/484,111

(22) PCT Filed: Jul. 10, 2002

(86) PCT No.: PCT/EP02/07658

§ 371 (c)(1),
(2), (4) Date: Jan. 15, 2004

(87) PCT Pub. No.: WO03/008390

PCT Pub. Date: Jan. 30, 2003

(65) Prior Publication Data

US 2004/0156786 A1 Aug. 12, 2004

(30) Foreign Application Priority Data

Jul. 17, 2001 (IT) .................. MI2001A01518

(51) Int. Cl.
*A61B 5/055* (2006.01)
(52) U.S. Cl. .................. 424/9.36; 424/9.3; 534/14; 534/15; 534/10; 540/450
(58) Field of Classification Search ........... 424/1.11, 424/1.65, 9.1, 9.3, 9.36, 9.361; 534/7, 10–16; 540/450
See application file for complete search history.

(56) References Cited

U.S. PATENT DOCUMENTS

| 3,107,260 | A | * | 10/1963 | Knell | .............. | 71/1 |
| 6,193,950 | B1 | * | 2/2001 | Platzek et al. | .............. | 424/9.36 |
| 6,403,055 | B1 | * | 6/2002 | Calabi et al. | .............. | 424/9.364 |

FOREIGN PATENT DOCUMENTS

GB 926351 5/1963

| WO | 92/09283 | * | 6/1992 |
| WO | WO98/05625 | | 2/1998 |

OTHER PUBLICATIONS

PCT International Search Report for PCT/EP02/07658 dated Oct. 10, 2002.
PCT International Preliminary Examination Report for PCT/EP02/07658 dated Aug. 5, 2003.
Caravan, P. et al: "Gadolinium(III) Chelates as MRI Contrast Agents: Structure, Dynamics, and Applications", Chemical Reviews, American Chemical Society, vol. 99, No. 9, Sep. 1999, pp. 2293-2352.

* cited by examiner

*Primary Examiner*—Dameron L. Jones
(74) *Attorney, Agent, or Firm*—Kramer Levin Naftalis & Frankel LLP

(57) ABSTRACT

Compounds of general formula (I): in which: $R_1$ is hydrogen, $C_1$–$C_{20}$ alkyl, $C_3$–$C_{10}$ cycloalkyl, $C_4$–$C_{20}$ cycloalkylalkyl, aryl, arylalkyl, or two R1, taken together, form a straight or cyclic $C_2$–$C_{10}$ alkylene group or an ortho disubstituted arylene; $R_2$ is hydrogen, $C_1$–$C_{20}$ alkyl, $C_3$–$C_{10}$ cycloalkyl, $C_4$–$C_{20}$ cycloalkylalkyl, aryl or aryl alkyl optionally substituted with functional groups which allow conjugation with a suitable molecule able to interact with physiological systems; $R_3$, $R_4$ and $R_5$ are hydrogen, $C_1$–$C_{20}$ alkyl, $C_3$–$C_{10}$ cycloalkyl, $C_4$–$C_{20}$ cycloalkylalkyl, aryl, arylalkyl; and their chelates with bi-trivalent ions of the metal elements having atomic number ranging between 20 and 31, 39, 42, 43, 44, 49, and between 57 and 83, and radioisotopes chosen among $^{203}$Pb $^{67}$Ga $^{68}$Ga $^{72}$As $^{111}$In $^{113}$In $^{90}$Y $^{97}$Ru $^{62}$Cu $^{64}$Cu $^{52}$Fe $^{52m}$Mn $^{140}$La $^{175}$Yb $^{153}$Sm $^{166}$Ho $^{149}$Pm $^{177}$Lu $^{142}$Pr $^{159}$Gd $^{212}$Bi $^{47}$Sc $^{149}$Pm $^{67}$Cu, $^{111}$Ag, $^{199}$Au, $^{161}$Tb and $^{51}$Cr as well as the salts thereof with physiologically compatible bases or acids (I)

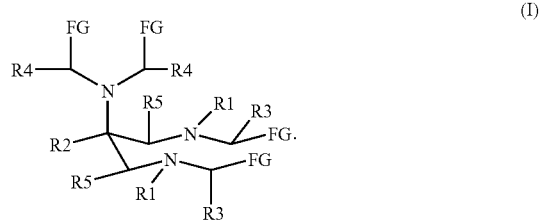

16 Claims, No Drawings

MULTIDENTATE AZA LIGANDS ABLE TO COMPLEX METAL IONS AND THE USE THEREOF IN DIAGNOSTICS AND THERAPY

This application is the national stage filing of corresponding international application number PCT/EP02/07658, filed Jul. 10, 2002, which claims priority of Italian Application No. MI2001A001518, filed Jul. 17, 2001.

The present invention relates to novel aza ligands able to complex metal ions, in particular paramagnetic ions, and the use of the corresponding complexes as contrast agents for magnetic resonance imaging (MRI).

A number of complexes of paramagnetic metal ions with cyclic and acyclic aza ligands are known as contrast agents in the MRI diagnostic technique (see for instance: The Chemistry of Contrast Agents in Medical Magnetic Resonance Imaging, Merbach A. E. and Toth E. Eds., John Wiley and sons, Chichester, 2001; Caravan P. et al. Chem. Rev. 1999, 99, 2293–2352 and U.S. Pat. Nos. 4,885,363; 4,916,246; 5,132,409; 6,149,890). Some of these complexes (Gd-DTPA, Gd-DOTA, Gd-HPDO3A, and the like) have recently been marketed.

The paramagnetic metal ions most extensively used in MRI diagnostics are either in the transitions metals and in the Lanthanide series. As far as Lanthanides are concerned, the attention is essentially focused on Gd(III) ion both for its high paramagnets (7 umpaired electrons) and for its favourable properties in terms of electronic relaxation. This metal does not possess any physiological function in mammalians, and its administration as free ion is strongly toxic even at low dosis (10–20 micromol/Kg). For this reason, it is necessary to use ligands that form chelates with the lanthanide ion endowed with high thermodynamic and kinetic stability. This means that the chelating ligand should exhibit a high level of affinity and selectivity for the relevant paramagnetic ions as opposed to the physiological ions. Moreover, the ligand should show suitable pharmacokinetic properties (excretion, binding to plasma proteins, metabolical inertia, and the like), and optimal relaxivity properties, that is to say that the values of this parameter should be and remain high, independently of the surrounding environment, in particular the presence of physiological anions and pH changes.

A novel class of ligands has now been found, which form complexes having particularly favorable characteristics, above all in terms of stability and relaxivity.

Relaxivity ($r_{1p}$) is an intrinsic property of paramagnetic complexes which characterizes their ability to increase the nuclear magnetic relaxation rate of vicinal protons. High relaxation rates ensure increased contrast in the image, which makes it possible to obtain physiological information in a short amount of time with obvious advantages in terms of both image quality and economic cost.

The relaxivity of a Gd(III) complex is a property directly related to the number (q) of water molecules of the inner coordination sphere of the metal ion. As said before, contrast agents for magnetic resonance imaging (MRI) are mostly represented by stable complexes of Gd(III) ions the large majority of which are based on octadentate ligands to ensure a high thermodynamic stability. This choice has however implied that only one water molecule may enter in the inner coordination sphere of the Gd(III) ion which has a coordination number of nine (The Chemistry of Contrast Agents in Medical Magnetic Resonance Imaging, Merbach A. E. and Toth E. Eds., John Wiley and sons, Chichester, 2001).

A further contribution to the observed relaxation rate (of the water protons in an aqueous solution containing a paramagnetic complex) derives from the exchange between the molecule(s) of coordinated water and the molecules of the remaining solvent. In particular, the increase of the observed relaxation rate is inversely related to the residence time ($\tau_M$) of the protons of the water molecule(s) which are coordinated to the paramagnetic center the inner coordination sphere. Higher relaxivity is obtained at fast exchange conditions.

The ligands of the invention forms complexes whose high starting relaxivity is consistent with the presence of two water molecules in the inner coordination sphere and with simultaneous favorable $\tau_M$ values.

The ligands of the invention have the following general formula (I):

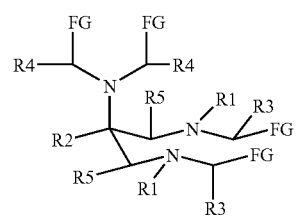

I in which:

$R_1$ is hydrogen, $C_1$–$C_{20}$ alkyl optionally substituted with one or more carboxy groups, $C_3$–$C_{10}$ cycloalkyl, $C_4$–$C_{20}$ cycloalkylalkyl, aryl, arylalkyl or the two $R_1$ groups, taken together, form a straight or cyclic $C_2$–$C_{10}$ alkylene group or an ortho-disubstituted arylene;

$R_2$ is hydrogen, $C_1$–$C_{20}$ alkyl, $C_3$–$C_{10}$ cycloalkyl, $C_4$–$C_{20}$ cycloalkylalkyl, aryl or arylalkyl optionally substituted with functional groups which allow conjugation with a suitable molecule able to interact with physiological systems;

$R_3$, $R_4$ and $R_5$, which can be the same or different, are hydrogen, $C_1$–$C_{20}$ alkyl, $C_3$–$C_{10}$ cycloalkyl, $C_4$–$C_{20}$ cycloalkylalkyl, aryl, arylalkyl;

FG, which can be the same or different, are carboxy, —$PO_3H_2$ or —RP(O)OH groups, wherein R is hydrogen, $C_1$–$C_{20}$ alkyl, $C_3$–$C_{10}$ cycloalkyl, $C_4$–$C_{20}$ cycloalkylalkyl, aryl, arylalkyl.

The invention further relates to the chelates of compounds of formula (I) with paramagnetic or radioactive metal ions, in particular with the bi-trivalent ions of the metal elements having atomic number ranging between 20 and 31, 39, 42, 43, 44, 49, and between 57 and 83, as well as the salts thereof with physiologically compatible bases or acids.

Particularly preferred for the diagnostic use as MRI contrast agents, are the complexes with paramagnetic ions such as $Fe^{2+}$, $Fe^{3+}$, $Cu^{2+}$, $Cr^{3+}$, $Gd^{3+}$, $Eu^{3+}$, $Dy^{3+}$, $La^{3+}$, $Yb^{3+}$ or $Mn^{2+}$, and in particular gadolinium complexes.

On the other hand, for uses in radiotherapy or radiodiagnostics, preferred complexes are those with $^{203}Pb$, $^{67}Ga$, $^{68}Ga$, $^{72}As$, $^{111}In$, $^{113}In$, $^{90}Y$, $^{97}Ru$, $^{62}Cu$, $^{64}Cu$, $^{52}Fe$, $^{52m}Mn$, $^{140}La$, $^{175}Yb$, $^{153}Sm$, $^{166}Ho$, $^{149}Pm$, $^{177}Lu$, $^{142}Pr$, $^{159}Gd$, $^{212}Bi$, $^{47}Sc$, $^{149}Pm$, $^{67}Cu$, $^{111}Ag$, $^{199}Au$, $^{161}Tb$ and $^{51}Cr$.

The chelates of the invention can also be in the form of salts, when the ligand has salifiable functions.

Preferred cations of inorganic bases which can be suitably used to salify the complexes of the invention comprise ions of alkali or alkaline-earth metals such as potassium, sodium, calcium, magnesium.

Preferred cations of organic bases comprise, inter alia, those of primary, secondary and tertiary amines such as ethanolamine, diethanolamine, morpholine, glucamine, N-methylglucaamine, N,N-dimethylglucamine.

Preferred anions of inorganic acids which can be suitably used to salify the complexes of the invention comprise the ions of halo acids such as chlorides, bromides, iodides or other ions such as sulfate.

Preferred anions of organic acids comprise those of acids routinely used in pharmaceutical technique for the salification of basic substances, such as acetate, succinate, citrate, fumarate, maleate, oxalate.

Preferred cations and anions of amino acids comprise, for example, those of taurine, glycine, lysine, arginine or ornithine or of aspartic and glutamic acids.

The $C_1$–$C_{20}$ alkyl group is a straight or branched group and preferably is a $C_1$–$C_6$ group, more preferably methyl, ethyl, propyl, isopropyl.

The $C_3$–$C_{10}$ cycloalkyl group is preferably a cyclopropyl, cyclopentyl or cyclohexyl group, optionally in turn substituted at one of the position of the ring, by an alkyl group as defined above.

The $C_4$–$C_{20}$ cycloalkylalkyl group is preferably cyclopropylmethyl, cyclohexylethyl, cyclohexylmethyl, cyclopentylmethyl, cyclopentylethyl.

Aryl is preferably phenyl or phenyl substituted with one to five substituents, which can be the same or different, selected from hydroxy, $C_1$–$C_2$ alkoxy, halogen, cyano, nitro, methyl, ethyl, carboxy, amino, $C_1$–$C_2$ alkyl- or dialkylamino, or alkyl groups variously substituted with one to three substituents such as hydroxy, $C_1$–$C_2$ alkoxy, halogen, cyano, nitro, methyl, ethyl, carboxy, amino, $C_1$–$C_2$ alkyl- or dialkylamino.

Ortho-disubstituted arylene is preferably optionally substituted 1,2-phenylene as indicated above.

$C_1$–$C_{20}$ Alkyl substituted with carboxy groups is preferably carboxymethyl.

FG is preferably a carboxy group.

$R_2$ is preferably methyl, alkyl as defined above or aryl, both optionally substituted with functional groups such as optionally protected carboxy, amino, formyl, hydroxy or mercapto, which can be used as conjugation sites with other compounds without interfering with the structural integrity of the molecule.

$R_3$ is preferably hydrogen.

$R_4$ is preferably hydrogen or methyl.

$R_5$ is preferably hydrogen.

Preferred compounds of formula (I) are those in which the two $R_1$ groups form together an alkylene, in particular ethylene or propylene, preferably ethylene, and the other groups are as defined for the general formula (I) or have the preferred meanings indicated above.

Compounds (I) in which $R_1$ is hydrogen, alkyl, cycloalkyl, cycloalkylalkyl or aryl can be prepared with a process which comprises:
a) reacting a compound (II)

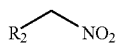
II wherein $R_2$ is as defined above, with formaldehyde and an amine (III)

$R_1$—$NH_2$      III wherein $R_1$ is as defined above, to give a compound of formula (IV)

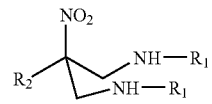
IV b) reducing the nitro group of compound (IV) to amino group, to give a compound of formula (V)

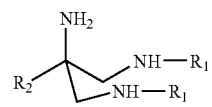
V reacting compounds of formula (V) with haloacetic acid esters, to give compounds (VI)

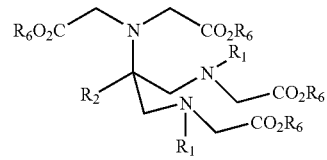
VI wherein $R_6$ is $C_1$–$C_6$ alkyl, and subsequent hydrolysis to give compounds (I), or reacting compounds (V) with formaldehyde and phosphorous acid or a compound of formula $RP(OH)_2$, wherein R is as defined above, to give the corresponding compounds (I) in which FG is —$PO_3H_2$ or $RP(O)OH$.

Compounds of formula (I) in which the two $R_1$ groups taken together form an alkylene group are obtained with a process comprising:
a) reacting a compound (II) with formaldehyde and a diamine of formula (VII)

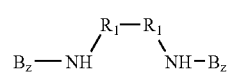
VII wherein $R_1$ is as defined above and Bz is benzyl or an amino-protective group, to give compound of formula (VIII)

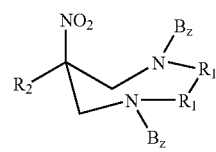
VIII b) reducing the nitro group and removing the benzyl groups, e.g. by catalytic hydrogenation, from compound (VIII) to give a compound of formula (IX)

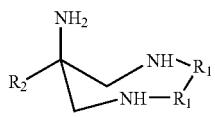

c) reacting (IX) with haloacetic acid esters to give a compound (X)

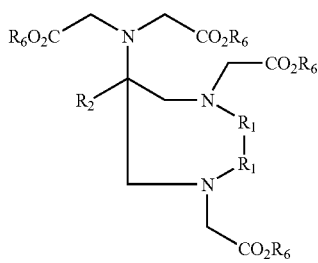

wherein $R_6$ is as defined above, or with formaldehyde and phosphorous acid or a compound of formula $RP(OH)_2$, wherein R is as defined above, to give the corresponding compounds (I) in which FG is $-PO_3H_2$ or $RP(O)OH$;

d) hydrolyzing the carboxy ester groups to give compounds (I) wherein the $R_1$ groups form together an alkylene.

Compounds of formula (I) in which both carboxylic groups and phosphonic groups are present, can be obtained by suitably changing the reactions sequences reported above, introducing the carboxymethyl or phosphonomethyl groups on the previously deprotected compound of formula (VIII), for example first by reaction with haloacetic esters, subsequent reduction of the nitro group and further reaction with formaldehyde and $H_3PO_3$ or $RP(OH)_2$, as described above, or viceversa. According to this procedure can also be prepared compounds of formula (I) in which the FG groups on the nitrogen atom of the ring are different from the FG groups present on the exocyclic amino group.

Amines of formula (IX), both in the protected and unprotected form, are novel and are a further object of the invention, as intermediates.

The compounds of the invention can further be conjugated with suitable molecules able to interact with physiological systems. Useful examples thereof, are bile acids, peptides, proteins, hormones, oligonucleotides and the like.

The complexes of compounds (I) can be administered as MRI contrast agents parenterally, preferably formulated as a sterile aqueous solution or suspension, whose pH can range for example from 6.0 to 8.5.

Said aqueous solutions or suspensions can be administered in concentrations ranging from 0.002 to 1.0 molar.

Said formulations can be freeze-dried and supplied as such, to be reconstituted prior to use. For the gastrointestinal use or for injection to body cavities, these agents can be formulated as a solution or suspension containing suitable additives in order to, for example, control viscosity.

For the oral administration they can be formulated according to preparation methods routinely used in pharmaceutical technique, optionally also as coated formulations to gain extra protection from the acid pH of the stomach, inhibiting the release of the chelated metal ion, which usually occurs at typical pH values of gastric juices.

Other excipients, such as sweetening agents and/o flavoring agents, can also be added according to known techniques of pharmaceutical formulation.

Paramagnetic Gd(III) complexes with ligands of formula (I) are endowed with a particularly good starting relaxivity which can be explained with the presence of two water molecules in the inner coordination sphere of said complexes and with simultaneous favorable fast exchange rate of coordinated water molecules.

It has been reported that for some Gd(III) complexes with q=2 (i.e. Gd-DO3A-like systems, a decrease in relaxivity was observed upon increasing of the solution pH. This decrease is most probably due to the fact that some anions present in the solution, such as the carbonate and hydroxyl ions, are in competition with the water molecules for the coordination sites on Gd(III) and, through the formation of ternary complexes with metal chelate, remarkably reduces the relaxivity thereof (S. Aime et al, *J.Biol.Inorg.Chem.*, 5, 488–497, (2000). Decrease in relaxivity is also observed when bidentate ligands are present in solution. Systems showing such behaviour are usually characterized by a small relaxation enhancement upon binding to proteins such as HSA. This is due to the replacement of the water molecules by donor atoms on the protein.

Conversely, tests performed with the Gd(III) complex of example 1 of the invention quite interestingly pointed out the ligands of the invention show a very low affinity for any anions and anionic metabolites present in solution.

This result strongly indicates that the relaxivity of the complex compounds of the invention is not "lowered" even in the presence of high concentrations of bidentate anions.

It further indicates that the ligands of the invention can advantageously be used to prepare paramnagnetic complex compounds with q=2, able to be conjugated to or to non-covalently interact with human serum albumin or other suitable macromolecules without that the donor atoms on said macromolecule, (for example, from aspartate or glutamate), could interact with the coordination sites of Gd(III) and induce a reduction of the attainable relaxivity.

Most probably, the substantial change in the ligands structure when compared with that of (DO3A) and of the corresponding DO3 MA trimethyl-derivate is responsible of the completely different behavior of the complex towards the bidentate anions.

The following examples illustrate the invention in greater detail.

EXAMPLE 1

1,4-Bis(carboxymethyl)-6-[bis(carboxymethyl)amino]-6-methylperhydro-1,4-diazepine

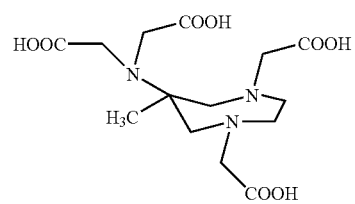

a) 1,4-Dibenzyl-6-methyl-6-nitroperhydro-1,4-diazepine

In a 250 mL round-bottom flask N,N'-dibenzylethylenediamine diacetate (18.4 g, 51.0 mmol) and nitroethane (3.66 mL, 50.9 mmol) are dissolved in ethanol (80 mL). Paraformaldehyde (5.00 g, 166.5 mmol) is added in portions to the solution and the resulting suspension is refluxed. The mixture becomes homogeneous (dissolution of paraformaldehyde) at about 60° C. and a slightly exothermic reaction takes place. After 3 h at reflux, the mixture is evaporated, taken up with aqueous saturated $Na_2CO_3$ solution and the organic product is repeatedly extracted with methylene chloride. The combined organic extracts are washed with water and dried over $Na_2SO_4$. After filtration and evaporation of methylene chloride, the waxy residue is purified by silica gel chromatography.

Elution with methylene chloride yields the pure title compound (15.65 g, 90.6%). Increasing the polarity of the eluent ($CH_2Cl_2$/MeOH 9:1), the acyclic derivative N,N'-dibenzyl-N-(2-nitropropyl)ethanediamine (0.350 g, 2.1%) is obtained.

Waxy white solid, m.p. 49.5–50° C. (n-hexane)
$^1$H-NMR ($CDCl_3$).
7.32 (m, 10H), 3.78 (d, 2H, J=13.2 Hz), 3.65 (d, 2H, J=13.2 Hz), 3.60 (d, 2H, J=14.1 Hz), 2.96 (d, 2H, J=14.1 Hz), 2.60 (m, 4H), 1.35 (s, 3H).
$^{13}$C-NMR ($CDCl_3$).
139.0 (s), 128.8 (d), 128.1 (d), 127.1 (d), 91.5 (s), 63.7 (t), 63.4 (t), 58.1 (t), 24.2 (q).
MS (CI) 340 (MH$^+$).
Anal. Calc. for $C_{20}H_{25}N_3O_2$ (339.43): C, 70.77; H, 7.42; N, 12.38. Found: C, 70.57; H, 7.60; N, 12.27.

b) 6-Amino-6-methylperhydro-1,4-diazepine

To a solution of the compound obtained in a) (6.00 g, 17.7 mmol) in a mixture of ethanol (45 mL) and water (5 mL) is added the catalyst consisting of 10% palladium on charcoal (1.0 g). The mixture is introduced in a Parr apparatus, hydrogenated at 28 atm (2.84 MPa) and room temperature. After 2 h, hydrogen is no longer absorbed. The reaction mixture is filtered through Celite®. The filtrate is evaporated to obtain the title compound (2.25 g, 98.3%) sufficiently pure for the subsequent step, in the form of a colorless oil.

$^1$H-NMR ($CDCl_3$).
2.82 (m, 4H), 2.63 (d, 2H, J=13.6 Hz), 2.57 (d, 2H, J=13.6 Hz), 1.86 (bs, 4H, exchange with $D_2O$), 0.96 (s, 3H).
$^{13}$C-NMR ($CDCl_3$).
62.2 (t), 53.8 (s), 51.7 (t), 26.5 (q).
MS (CI) 130 (MH$^+$).
Anal. Calc. for $C_6H_{15}N_3$ (129.21): C, 55.78; H,111.70; N, 32.52. Found: C, 55.56; H, 11.91; N, 32.29.

c) 1,4-Bis(t-butoxycarbonylmethyl)-6-[bis(t-butoxycarbonylmethyl)amino]-6-methylperhydro-1,4-diazepine To a solution of the compound obtained in b) (0.909 g, 7.04 mmol) in dry acetonitrile (25 mL), powdered potassium carbonate (6.53 g, 47.24 mmol) and sodium sulfate (ca. 3 g) are added. After cooling to 0–5° C. (ice bath) t-butyl bromoacetate (4.50 mL, 30.45 mmol) is added in 10 minutes and the mixture is left at this temperature for 15 minutes. Subsequently, the reaction mixture is refluxed for 4 hours, then cooled to room temperature, inorganic salts are filtered off and the filtrate is evaporated under vacuum. The resulting residue is purified by "flash" chromatography on silica gel. Elution with n-hexane/ethyl acetate 8:2 yields the pure title compound (3.15 g, 76.4%) as colorless oil.

$^1$H-NMR ($CDCl_3$).
3.68 (s, 4H), 3.27 (s, 4H), 3.03 (d, 2H, J=14.1 Hz), 2.72 (m, 4H), 2.61 (d, 2H, J=14.1 Hz), 1.44 (s, 36H), 1.09 (s, 3H).
$^{13}$C-NMR ($CDCl_3$).
172.6 (s), 170.8 (s), 80.6 (s), 80.1 (s), 66.1 (t), 62.3 (t), 60.6 (s), 59.1 (t), 51.5 (t), 28.1 (q), 28.0 (q), 24.1 (q).
MS (CI) 586 (MH$^+$).

Anal. Calc. for $C_{30}H_{55}N_3O_8$ (585.78): C, 61.51; H, 9.46; N, 7.17. Found: C, 61.42; H, 9.62; N, 6.98.

d) 1,4-Bis(carboxymethyl)-6-[bis(carboxymethyl)amino]-6-methylperhydro-1,4-diazepine In a 50 mL round-bottom flask, the ester obtained in c) (3.03 g, 5.17 mmol) is dissolved in trifluoroacetic acid (10 mL). The resulting solution is left at room temperature overnight, then is evaporated under vacuum, concentrated HCl is added and evaporated to dryness. The solid residue is loaded on an Amberlite® XAD1600 resin column (3 cm ID×30 cm). Elution with water/acetone (100/0→70/30) yields the pure title compound (1.33 g, 71.1%) as white crystals, m.p. 178–181° C. (dec.) ($H_2O$).

$^1$H-NMR ($D_2O$).
3.65 (s, 8H), 3.51 (m, 4H), 3.38 (m, 4H), 1.06 (s, 3H)
$^{13}$C-NMR ($D_2O$).
175.9 (s), 173.3 (s), 65.7 (s), 61.2 (t), 61.1 (t), 56.1 (t), 54.3 (t), 19.5 (q).
MS (FAB+) 362 (MH$^+$).
Anal. Calc. for $C_{14}H_{23}N_3O_8$ (361.35): C, 46.53; H, 6.42; N, 11.63. Found: C, 46.56; H, 6.70; N, 11.39.

Operating analogously to the procedure described above, the following compounds can be obtained:

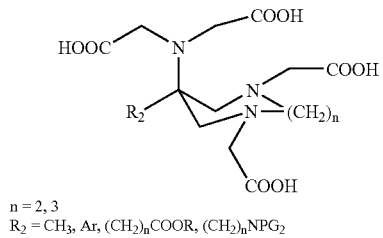

n = 2, 3
$R_2 = CH_3$, Ar, $(CH_2)_nCOOR$, $(CH_2)_nNPG_2$

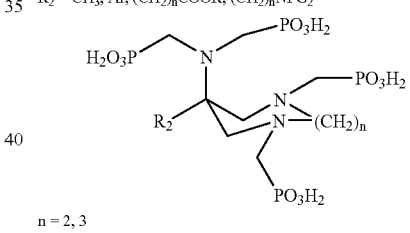

n = 2, 3
$R_2 = CH_3$, Ar, $(CH_2)_nCOOR$, $(CH_2)_nNPG_2$

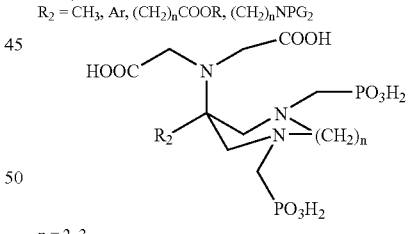

n = 2, 3
$R_2 = CH_3$, Ar, $(CH_2)_nCOOR$, $(CH_2)_nNPG_2$

In particular the following ligands were prepared:

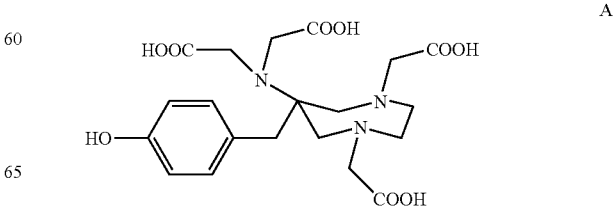

A

-continued

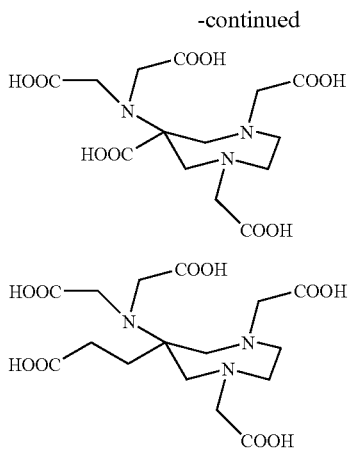

e) Gd(III) Complex of 1,4-Bis(carboxymethylmethyl)-6-[bis(hydroxycarbonylmethyl)amino]-6-methylperhydro-1,4-diazepine In a 100 mL round-bottom flask, the ligand from d) (3.61 g, 10 mmol) is suspended in 30 mL of $H_2O$, 1N NaOH (10 mL) is added to obtain a clear solution, to which $Gd_2O_3$ (1.81 g, 5 mmol) and heated at 50° C. for 15 hours: After cooling at room temperature, the solution is filtered and evaporated to dryness to obtain a white solid.

Anal. Calc. for $C_{14}H_{19}GdN_3NaO_8$ (537.56): C, 31.28; H, 3.56; N, 7.82; Na 4.28; Gd 29.25. Found: C, 30.98; H, 3.71; N, 7.99; Na 4.01; Gd 29.59.

EXAMPLE 2

N,N''-diisopropyl-2-methyl-1,2,3-propanetriamino-N,N',N',N''-tetraacetic acid

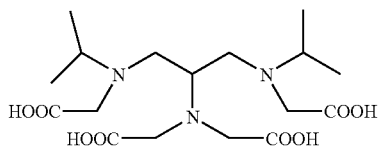

a) N,N'-Diisopropyl-2-methyl-2-nitro-1,3-propanediamine

A 250 mL round-bottom flask containing isopropylamine (20.6 g, 349 mmol) is cooled to 3–5° C. on ice bath and 37% aqueous formaldehyde solution (26.3 mL, 350 mmol) is added in about 30 min so that the reaction temperature does not exceed 10° C. After completion of the addition, the mixture is stirred for 15 minutes, then nitroethane (13.1 g, 174.5 mmol) is added in a single portion. The mixture is left to warm to room temperature, then $Na_2SO_4$ (20 g) is added, stirring to complete dissolution. The two phases formed are separated and the lower aqueous layer is discarded. Further $Na_2SO_4$ (20 g) is added to the organic phase and left to stand for 60 hours. The mixture is filtered and the solid is repeatedly washed with diethyl ether. Filtrate and washings are combined and evaporated under vacuum. The residue is distilled under vacuum, collecting the fraction which distils at 88–90° C. under 3 mmHg, corresponding to the title product (25.9 g, 68.2%) as a colorless oil, p.eb. 88–90° C. (3 mmHg).

$^1$H-NMR ($CDCl_3$).
1.01 (d, 12H, J=6.2 Hz), 1.50 (bs, 2H, exchanges with $D_2O$), 1.55 (s, 3H), 2.73 (sept, 2H, J=6.2 Hz), 2.99 (AB, 4H, J=12.8 Hz).
$^{13}$C-NMR ($CDCl_3$).
20.7 (q), 22.8 (q), 48.9 (t), 52.5 (d), 91.9 (s).
MS (CI) 218 ($MH^+$).
Anal. Calc. for $C_{10}H_{23}N_3O_2$ (217.31): C, 55.27; H, 10.67; N 19.34. found: C, 55.11; H, 10.81; N, 19.39.

b) N,N''-Diisopropyl-2-methyl-1,2,3-propanetriamine

To a solution of the compound obtained in a) (18.50 g, 85.1 mmol) in $CH_3OH$ (100 mL), Nickel Raney 50% in $H_2O$ (3.5 g) is added. The mixture is placed into a Parr apparatus and hydrogenated at 60 atm and room temperature. After about 3 h no more hydrogen absorption is observed. The mixture is filtered through Celite® and the residue is washed with $CH_3OH$ (2×15 mL). Filtrate and washings are combined and evaporated. The residue is distilled under vacuum, collecting the fraction distilling at 98–100° C. under 3 mmHg, corresponding to the title product (15.15 g, 95.0%), which is a lightly yellow clear oil, p.eb. 88–90° C. (3 mmHg).

$^1$H-NMR ($CDCl_3$).
1.02 (s, 3H), 1.03 (d, 12H, J=6.2 Hz), 1.40 (bs, 4H, exchanges with $D_2O$), 2.46 (AB, 4H, J=11.6 Hz), 2.71 (sept, 2H, J=6.2 Hz).
$^{13}$C-NMR ($CDCl_3$).
22.9 (q), 25.4 (q), 49.2 (t), 51.6 (s), 56.9 (d).
MS (CI) 188 ($MH^+$).
Anal. Calc. for $C10H_{25}N_3$ (187.33): C, 64.12; H, 13.45; N, 22.43. Found: C, 63.89; H, 13.61; N, 22.49.

c) N,N''-Diisopropyl-N,N',N',N''-tetrakis(t-butoxycarbonylmethyl)-2-methyl-1,2,3-propanetriamine To a solution of the triamine from b) (1.25 g, 6.67 mmol) in acetonitrile (10 mL), N,N-diisopropylethylamine (11.6 mL, 66.6 mmol) is added. t-Butyl bromoacetate (5.90 mL, 36.5 mmol) is added dropwise in 30 minutes under stirring and cooling on ice bath; after completion of the addition the ice bath is removed and the mixture is left at room temperature for further 30 minutes, then refluxed for 15 hours. After that, the mixture is cooled and evaporated under vacuum. The residue is partitioned between $CH_2Cl_2$ and a 10% aqueous $Na_2CO_3$ solution, and the aqueous phase is further extracted with $CH_2Cl_2$ (2×20 mL). The organic phases are dried over $Na_2SO_4$, filtered and evaporated under vacuum. The residue is purified by column chromatography ($SiO_2$, gradient hexane/$Et_2O$ 100/0→50/50, 30 mL fractions) to obtain the pure title tetraester (3.57 g, 83.0%) as a slightly yellow clear oil.

Rf ($SiO_2$, $CHCl_3$) 0.70.
$^1$H-NMR ($CDCl_3$).
0.91 (d, 6H, J=6.6 Hz), 0.96 (d, 6H, J=6.8 Hz), 1.16 (s, 3H), 1.41 (s, 36H), 2.57 (AB, 4H, J=14.3 Hz), 2.87 (sept, 2H, J=6.6 Hz), 3.38 (s, 4H), 20 3.52 (s, 4H).
$^{13}$C-NMR ($CDCl_3$).
17.7 (q), 19.8 (q), 19.9 (q), 27.9 (q), 51.2 (s), 53.9 (t), 54.0 (t), 55.0 (t), 63.1 (d), 79.7 (d), 80.0 (s), 172.0 (s), 172.9 (s).
MS (EI) 645, 644 ($MH^+$), 530, 457, 343, 287, 231, 186, 160, 130, 112, 25 88, 70.
Anal. Calc. for $C_{34}H_{65}N_3O_8$ (643.91): C, 63.42; H, 10.18; N, 6.53. found: C, 63.29; H, 10.33; N, 6.39.

d) N,N''-Diisopropyl-2-methyl-1,2,3-propaneriamino-N,N',N',N''-tetraacetic acid

The ester from c) (5.96 g, 9.10 mmol) is placed in a 100 mL round-bottom flask and concentrated hydrochloric acid (20 mL) is added. The mixture is refluxed for 7 hours, then cooled, diluted with $H_2O$ (20 mL) and extracted with $CH_2Cl_2$ (3×15 mL). The aqueous phase is evaporated to dryness; the residue is recrystallized from conc. HCl/ethanol, to yield the title ligand as dihydrochloride (4.08 g, 91.0%).

$^1$H-NMR ($CDCl_3$)

1.14 (d, 6H, J=6.3 Hz), 1.17 (d, 6H, J=6.3 Hz), 1.33 (s, 3H), 3.21 (AB, 4H, J=15.1 Hz), 3.57 (sept, 2H, J=6.3 Hz), 3.68 (s, 8H).

MS ($FAB^+$) 420 ($MH^+$), 442 ($MNa^+$), 458 ($MK^+$) [Calc. for $C_{18}H_{33}N_3O_8$: 419.47].

Anal. Calc. for $C_{18}H_{33}N_3O_8$. 2HCl (492.39): C, 43.91; H, 7.16; N, 8.57. Found: C, 43.66; H, 7.30; N, 8.41.

MS ($FAB^+$) 420 ($MH^+$), 442 ($MNa^+$), 458 ($MK^+$) [Calc. for $Cl_8H_{33}N_3O_8$: 419.47].

Anal. Calc. for $C_{18}H_{33}N_3O_8$. 2HCl (492.39): C, 43.91; H, 7.16; N, 8.57. Found: C, 43.66; H, 7.30; N, 8.41.

EXAMPLE 3

Stability Properties of the Gd(III) Complex of Example 1.

1.5 Potentiometric Measurements

All the pH metric measurements (pH=–log [$H^+$]) were carried out in degassed 0.1 mol $dm^{-3}$ $NMe_4NO_3$ solutions, at 298.1 K, by using a Metrohm 670 Titroprocessor equipped with a Metrohm 6.0203.100 combined pH electrode. Prior to each potentiometric titration, the combined Metrohm electrode was calibrated as a hydrogen concentration probe by titrating known amounts of HCl with $CO_2$-free $NMe_4OH$ solutions and determining the equivalent point by the Gran's method which allows to determine the standard potential E°, and the ionic product of water. In the complexation experiments the metal ion concentration was about 80% of the ligand concentration. At least three measurements (about 100 data points each one) were performed for each system in the pH range 2.5–10.5 and the relevant e.m.f. data were treated by means of the computer programs SUPERQUAD and HYPERQUAD which furnished the protonation and the complexation constants.

| Reaction | Log $K_H$ |
|---|---|
| H + L = HL | 11.80 (2) |
| HL + H = $H_2L$ | 6.55 (2) |
| $H_2L$ + H = $H_3L$ | 4.09 (3) |
| $H_3L$ + H = $H_4L$ | 2.60 (3) |
| $H_4L$ + H = $H_5L$ | 1.44 (4) |

| Reaction | Log$K_{Gd}$ |
|---|---|
| M + L = ML | 21.52(1) |

Log$K_{Gd}$ (conditional, pH 7.4)=17.06

Relaxometric Properties of the Gd(III) Complex of Example 1.

The relaxivity determined at 25° C., pH 7 and 20 MHz for said complex is 7.1 $mM^{-1}s^{-1}$.

The exchange time ($\tau_M$) value of the Gd(III) complex of the example 1 has been assessed by measuring the transverse water $^{17}O$ NMR relaxation time at variable temperature according to the procedure described by Aime et al., in the above cited literature. The results are included in FIG. 1. Obtained value turned out to be 90 ns at 298 K. Albeit the optimal value (about 30 ns) has not been attained, this exchange rate can be considered quite fast, especially if compared with that of (Gd-DO3A), the Gd(III) complex of reference, with two water molecules in the inner sphere, whose $\tau_M$ value is 160 ns.

FIG. 2 shows the NMRD profile of the Gd(III) complex of the example 1, from whose fitting we could calculate a $\tau_R$ (the molecular reorientational time) value of 80 ps and electronic relaxation time values similar to those of other small-sized Gd(III) complexes (see Merbac A. E., cited above).

The relaxivity of this complex was further tested as a function of the pH. FIG. 3 shows the obtained results.

Surprisingly enough, the relaxation rate of the tested complex compound was found to be substantially constant over all the investigated pH range. This result clearly indicates that the Gd complex with the ligands of the invention shows a low affinity for hydroxyl and carbamate anions present in solution at basic pH. On the contrary, they would have remarkably reduced the measured relaxivity.

A test, to further evaluate the lack of formation of ternary complexes was performed. As a non-limiting example, we measured the affinity of the compound of example 1 for lactate and phosphate ions. The determination was performed directly by adding increasing amounts of each anion to a 1 mM solution of the Gd(III) complex. The obtained results, shown in FIG. 4, indicate the complete absence of interaction even in presence of high concentration of bidentate endogenous anions.

Conversely analogous titrations of Gd-DO3A and Gd-DO3MA (both endowed with q=2) with lactate ions yielded $K_A$ values of 150 $M^{-1}$ and 110 $M^{-1}$, respectively.

The Gd complex of Ligand 1, which does not show any measurable association constant, is definitely the complex having lower affinity for this anion.

This result shows that the relaxivity of the Gd-complexes with the ligands of the invention is not "lowered" even in the presence of high concentrations of bidentate endogenous anions.

Furthermore, the high exchange rate of coordinated water makes this type of paramagnetic complexes particularly interesting for obtaining high relaxivities (r1 and/or r2) once their molecular motion is slowed for example through binding with macromolecules. As it is known by those skilled in the art, a number of procedures are available to carry out the binding (both covalent and non-covalent) of a ligand and/or of a metal complex thereof (both covalent and non-covalent) with the concerned molecules.

What is claimed is:

1. A compound of general formula (I):

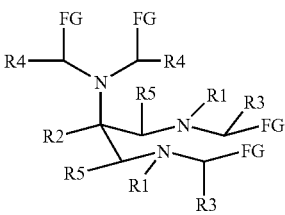

in which:

$R_1$ is hydrogen, $C_1$–$C_{20}$ alkyl, $C_3$–$C_{10}$ cycloalkyl, $C_4$–$C_{20}$ cycloalkylalkyl, aryl, arylalkyl; or the two $R_1$ groups, taken together, form a straight or cyclic $C_2$–$C_{10}$ alkylene group or an ortho-disubstituted arylene;

$R_2$ is hydrogen, $C_1$–$C_{20}$ alkyl, $C_3$–$C_{10}$ cycloalkyl, $C_4$–$C_{20}$ cycloalkylalkyl, aryl or arylalkyl optionally substituted with functional groups which allow conjugation with a suitable molecule able to interact with physiological systems;

$R_3$, $R_4$ and $R_5$, which are the same or different, are hydrogen, $C_1$–$C_{20}$ alkyl, $C_3$–$C_{10}$ cycloalkyl, $C_4$–$C_{20}$ cycloalkylalkyl, aryl, arylalkyl;

FG, which are the same or different, are carboxy, —$PO_3H_2$ or —RP(O)OH groups, wherein R is hydrogen, $C_1$–$C_{20}$ alkyl, $C_3$–$C_{10}$ cycloalkyl, $C_4$–$C_{20}$ cycloalkylalkyl, aryl, arylalkyl; or their chelates with bi-trivalent ions of the metal elements having atomic numbers ranging between 20 and 31, 39, 42, 43, 44, 49, or between 57 and 83, and radioisotopes $^{203}$Pb, $^{67}$Ga, $^{68}$Ga, $^{72}$As, $^{111}$In, $^{113}$In, $^{90}$Y, $^{97}$Ru, $^{62}$Cu, $^{64}$Cu, $^{52}$Fe, $^{52}$Mn, $^{140}$La, $^{175}$Yb, $^{153}$Sm, $^{166}$Ho, $^{149}$Pm, $^{177}$Lu, $^{142}$Pr, $^{159}$Gd, $^{212}$Bi, $^{47}$Sc, $^{149}$Pm, $^{67}$Cu, $^{111}$Ag, $^{199}$Au, $^{161}$Tb, and $^{51}$Cr as well as salts thereof with physiologically compatible bases or acids.

2. A compound of claim 1, wherein one or more of FG is a carboxy group.

3. A compound of claim 1 wherein $R_2$ is a $C_1$–$C_{20}$ alkyl or aryl group.

4. A compound of claim 1, wherein $R_3$ is hydrogen, $R_4$ is hydrogen or methyl, and $R_5$ is hydrogen.

5. A compound of claim 1, wherein the two $R_1$ groups together form an alkylene.

6. A compound of claim 5, wherein the two $R_1$ groups together form an ethylene group.

7. An MRI contrast agent comprising a chelate of the compound of claim 1 complexed with a metal ion.

8. The MRI contrast agent of claim 7, wherein the metal ion is selected from the group consisting of Gd($^{3+}$), Eu($^{3+}$), Dy($^{3+}$), La($^{3+}$), Yb($^{3+}$) and Mn($^{3+}$).

9. A compound of claim 8 wherein the metal ion is Gadolinium.

10. A radiotherapeutic or radiodiagnostic agent comprising a chelate of the compound of claim 1 complexed with a radioisotope.

11. A pharmaceutical or diagnostic composition comprising a compound of claim 1 in admixture with a suitable carrier.

12. A compound of formula (IX):

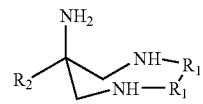

IX wherein the two $R_1$ groups form a straight or cyclic $C_2$–$C_{10}$ alkylene group or an ortho-disubstituted arylene and $R_2$ is hydrogen, $C_1$–$C_{20}$ alkyl, $C_3$–$C_{10}$ cycloalkyl, $C_4$–$C_{20}$ cycloalkylalkyl, aryl or arylalkyl optionally substituted with functional groups which allow conjugation with a suitable molecule able to interact with physiological systems.

13. A compound of claim 12, wherein the two $R_1$ groups together form an ethylene or propylene group.

14. A compound of claim 3, wherein said alkyl or aryl group is substituted with one or more carboxy or amino groups.

15. A compound of claim 14, wherein said carboxy or amino groups are protected.

16. A compound of claim 14, wherein said alkyl group is a methyl group.

* * * * *